US012611191B2

(12) United States Patent
Martins

(10) Patent No.: US 12,611,191 B2
(45) Date of Patent: Apr. 28, 2026

(54) ULTRASOUND IMAGING SYSTEM FOR GENERATING A BLENDED IMAGE INCLUDING HARMONIC IMAGE DATA FROM A HARMONIC IMAGE AND FUNDAMENTAL IMAGE DATA FROM A FUNDAMENTAL IMAGE BASED ON DETERMINING A TRANSITION ZONE AT WHICH TO BLEND THE HARMONIC IMAGE AND THE FUNDAMENTAL IMAGE

(71) Applicant: GE Precision Healthcare LLC, Waukesha, WI (US)

(72) Inventor: Bo Martins, Rodovre (DK)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/904,212

(22) Filed: Oct. 2, 2024

(65) Prior Publication Data

US 2026/0090792 A1     Apr. 2, 2026

(51) Int. Cl.
*A61B 8/00*          (2006.01)
*G16H 40/63*         (2018.01)

(52) U.S. Cl.
CPC ............ *A61B 8/5246* (2013.01); *A61B 8/463* (2013.01); *A61B 8/5269* (2013.01); *A61B 8/54* (2013.01); *G16H 40/63* (2018.01)

(58) Field of Classification Search
None
See application file for complete search history.

(56) References Cited

U.S. PATENT DOCUMENTS

| | | | | |
|---|---|---|---|---|
| 5,879,303 | A * | 3/1999 | Averkiou | ............ G01S 7/52036 |
| | | | | 600/447 |
| 6,283,919 | B1 | 9/2001 | Roundhill et al. | |
| 6,458,083 | B1 | 10/2002 | Jago et al. | |
| 6,514,206 | B2 | 2/2003 | Maxwell et al. | |
| 6,656,123 | B2 | 12/2003 | Jensen et al. | |
| 8,454,516 | B1 | 6/2013 | Roundhill et al. | |
| 10,779,800 | B2 | 9/2020 | Martins | |
| 10,925,585 | B2 | 2/2021 | Jong | |
| 10,952,703 | B2 | 3/2021 | Adams et al. | |
| 11,782,146 | B2 | 10/2023 | Martins | |

(Continued)

FOREIGN PATENT DOCUMENTS

| | | |
|---|---|---|
| CN | 103202713 B | 7/2013 |
| CN | 104546008 B | 4/2015 |

(Continued)

*Primary Examiner* — Nyrobi Celestine
(74) *Attorney, Agent, or Firm* — SPQ IP LLC

(57) ABSTRACT

Various systems and methods are provided for generating a blended image including harmonic image data from a harmonic image and fundamental image data from a fundamental image. An ultrasound probe may be controlled to acquire a fundamental image of a region of interest of a subject and a harmonic image of the region of interest of the subject. A transition zone at which to blend the harmonic image and the fundamental image may be determined. A blended image including harmonic image data from the harmonic image and fundamental image data from the fundamental image may be generated based on determining the transition zone. A display may be controlled to display the blended image.

17 Claims, 15 Drawing Sheets

400

CONTROL AN ULTRASOUND PROBE TO ACQUIRE NOISE IMAGE DATA — 410

GENERATE A NOISE IMAGE BASED ON THE NOISE IMAGE DATA — 420

DETERMINE A TRANSITION ZONE AT WHICH TO BLEND A HARMONIC IMAGE AND A FUNDAMENTAL IMAGE BASED ON THE NOISE IMAGE — 430

(56)     References Cited

U.S. PATENT DOCUMENTS

| | | | | |
|---|---|---|---|---|
| 2014/0066768 | A1 | 3/2014 | Sui et al. | |
| 2015/0265252 | A1* | 9/2015 | Chu | A61B 8/461 |
| | | | | 600/431 |
| 2018/0000452 | A1* | 1/2018 | Adams | G01S 7/52095 |
| 2018/0153521 | A1* | 6/2018 | Martins | A61B 8/5269 |
| 2018/0330518 | A1* | 11/2018 | Choi | A61B 8/14 |
| 2024/0338800 | A1* | 10/2024 | Xia | A61B 8/5269 |

FOREIGN PATENT DOCUMENTS

| | | |
|---|---|---|
| CN | 104586433 B | 5/2015 |
| CN | 105982695 A | 10/2016 |
| JP | H1017958 A | 7/1998 |

* cited by examiner

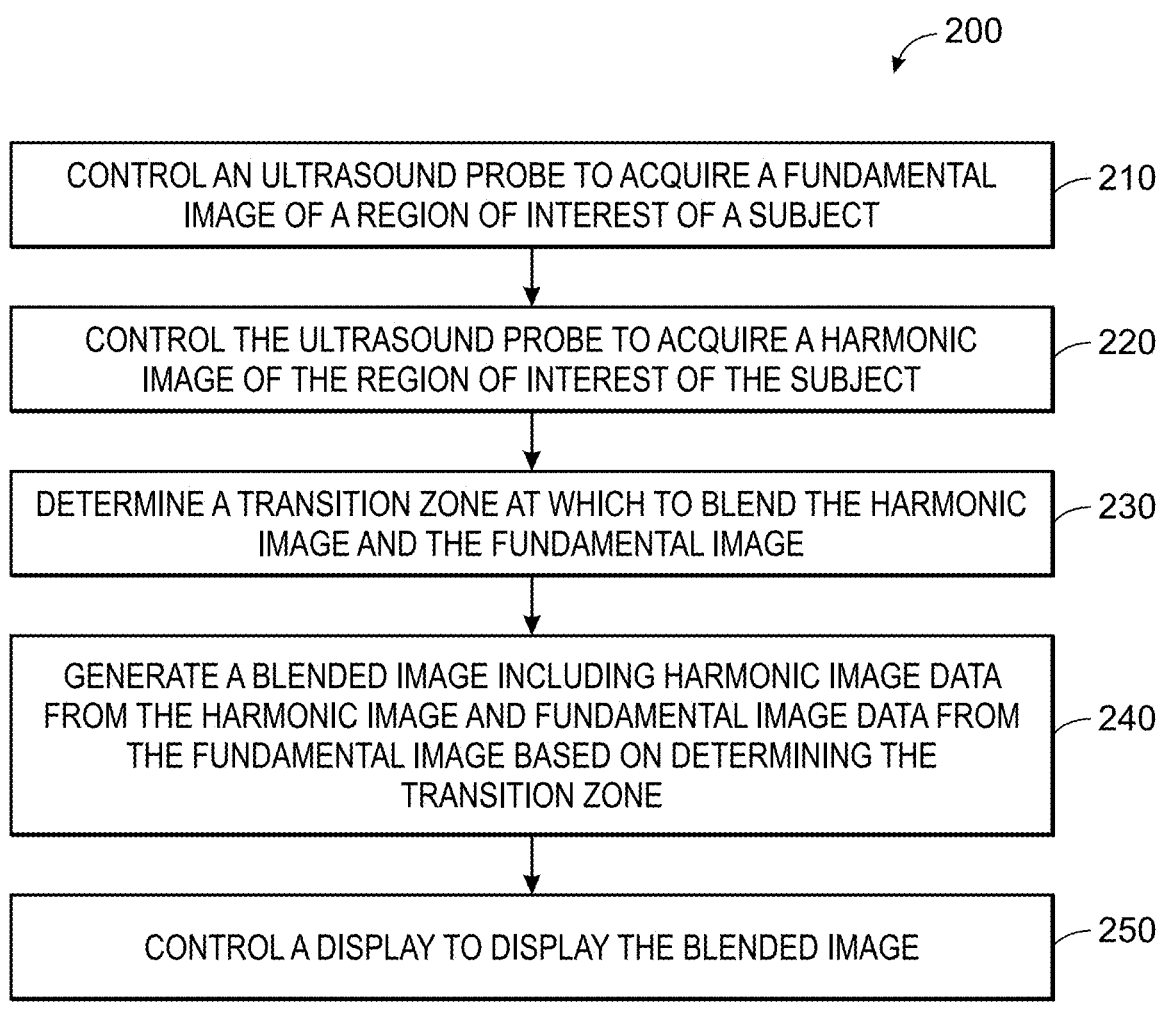

200

CONTROL AN ULTRASOUND PROBE TO ACQUIRE A FUNDAMENTAL IMAGE OF A REGION OF INTEREST OF A SUBJECT ⌐ 210

CONTROL THE ULTRASOUND PROBE TO ACQUIRE A HARMONIC IMAGE OF THE REGION OF INTEREST OF THE SUBJECT ⌐ 220

DETERMINE A TRANSITION ZONE AT WHICH TO BLEND THE HARMONIC IMAGE AND THE FUNDAMENTAL IMAGE ⌐ 230

GENERATE A BLENDED IMAGE INCLUDING HARMONIC IMAGE DATA FROM THE HARMONIC IMAGE AND FUNDAMENTAL IMAGE DATA FROM THE FUNDAMENTAL IMAGE BASED ON DETERMINING THE TRANSITION ZONE ⌐ 240

CONTROL A DISPLAY TO DISPLAY THE BLENDED IMAGE ⌐ 250

CONTROL AN ULTRASOUND PROBE TO ACQUIRE NOISE IMAGE DATA ⌐ 410

GENERATE A NOISE IMAGE BASED ON THE NOISE IMAGE DATA ⌐ 420

DETERMINE A TRANSITION ZONE AT WHICH TO BLEND A HARMONIC IMAGE AND A FUNDAMENTAL IMAGE BASED ON THE NOISE IMAGE ⌐ 430

CONTROL AN ULTRASOUND PROBE TO ACQUIRE TIME GAIN COMPENSATION (TGC) DATA — 510

GENERATE A TGC MATRIX BASED ON THE TGC DATA — 520

DETERMINE A TRANSITION ZONE AT WHICH TO BLEND A HARMONIC IMAGE AND A FUNDAMENTAL IMAGE BASED ON A NOISE IMAGE AND THE TGC MATRIX — 530

ULTRASOUND IMAGING SYSTEM FOR GENERATING A BLENDED IMAGE INCLUDING HARMONIC IMAGE DATA FROM A HARMONIC IMAGE AND FUNDAMENTAL IMAGE DATA FROM A FUNDAMENTAL IMAGE BASED ON DETERMINING A TRANSITION ZONE AT WHICH TO BLEND THE HARMONIC IMAGE AND THE FUNDAMENTAL IMAGE

TECHNICAL FIELD

The present disclosure relates to ultrasound imaging system for acquiring a fundamental image of a region of interest of a subject and a harmonic image of the region of interest of the subject, and generating a blended image including harmonic image data from the harmonic image and fundamental image data from the fundamental image. More specifically, the present disclosure relates to an ultrasound imaging system for determining a transition zone at which to blend the harmonic image and the fundamental image, and generating the blended image based on the determined transition zone.

BACKGROUND

An ultrasound imaging system may include an ultrasound probe that is configured to transmit ultrasound signals towards a region of interest and receive echo signals reflected by the region of interest. The ultrasound probe may transmit the ultrasound signals using a spectral band including a fundamental frequency. The ultrasound probe may receive echo signals having the fundamental frequency and echo signals having harmonic frequencies of the fundamental frequency. Generally, the harmonic frequencies are integer multiples of the fundamental frequency. For instance, if the fundamental frequency is 4 megahertz (MHz), then the second harmonic frequency is 8 MHz, the third harmonic frequency is 12 MHz, etc.

An ultrasound imaging system may use a fundamental imaging technique in which a fundamental image is generated using echo signals having the fundamental frequency of the transmitted ultrasound signals. In other situations, an ultrasound imaging system may use a harmonic imaging technique in which a harmonic image is generated using echo signals having harmonic frequencies of the fundamental frequency of the transmitted ultrasound signal. For example, an ultrasound imaging system may use tissue harmonic imaging in which a harmonic image is generated using echo signals having the second harmonic frequency of the fundamental frequency of the transmitted ultrasound signal. As another example, an ultrasound imaging system may use superharmonic imaging in which a harmonic image is generated using echo signals having the third harmonic frequency, the fourth harmonic frequency, and the fifth harmonic frequency of the fundamental frequency of the transmitted ultrasound signal.

A harmonic image may include increased lateral resolution, increased axial resolution, and increased signal to noise ratio as compared to a fundamental image. However, a fundamental image may include increased quality at particular depths due to lower attenuation of the echo signals of the fundamental frequency of the transmitted ultrasound signal. Accordingly, in some cases, a harmonic image may have certain areas that are of higher quality than a fundamental image, and may have certain areas that are of lower quality than a fundamental image, and vice versa. In some cases, an ultrasound imaging system may acquire a harmonic image of the region of interest and a fundamental image of the region of interest, and simultaneously display the harmonic image and the fundamental image of the region of interest. However, in these cases, the simultaneous display utilizes an increased portion of the display screen, and/or requires an operator to view both of the displayed images.

An ultrasound imaging system may generate a blended image of a region of interest in which harmonic image data of a harmonic image of the region of interest is blended with fundamental image data of a fundamental image of the region of interest. For example, the ultrasound imaging system may be configured to use harmonic image data from the harmonic image at shallow depths up to a first predetermined depth, use harmonic image data from the harmonic image and fundamental image data from the fundamental image at intermediate depths between the first predetermined depth and a second predetermined depth, and use fundamental image data from the fundamental image at deeper depths beyond the second predetermined depth. As another example, the ultrasound imaging system may use harmonic image data from the harmonic image up to a predetermined depth, and use fundamental image data from the fundamental image beyond the predetermined depth. In the foregoing cases, the blended image might appear artificial because the switch from the harmonic image data to the fundamental image data may be highly noticeable. In other cases, the predetermined depth, or predetermined depths, that is used to switch from the harmonic image data to the fundamental image data might correspond to an unsuitable region for switching between the different imaging data. For instance, the harmonic image data might be of higher quality than the fundamental image data beyond the predetermined depth, or vice versa. Accordingly, the display of the blended image might not be intuitive to the operator, and/or might be of low quality.

SUMMARY

This summary introduces concepts that are described in more detail in the detailed description. It should not be used to identify essential features of the claimed subject matter, nor to limit the scope of the claimed subject matter.

In an aspect, an ultrasound imaging system may include an ultrasound probe; a display; and one or more processors configured to: control the ultrasound probe to acquire a fundamental image of a region of interest of a subject; control the ultrasound probe to acquire a harmonic image of the region of interest of the subject; determine a transition zone at which to blend the harmonic image and the fundamental image; generate a blended image including harmonic image data from the harmonic image and fundamental image data from the fundamental image based on determining the transition zone; and control the display to display the blended image.

The one or more processors may further be configured to generate a noise image based on noise image data acquired by the ultrasound probe. The determining the transition zone may include determining the transition zone based on the noise image.

The one or more processors may further be configured to generate a time gain compensation (TGC) matrix based on TGC data acquired by the ultrasound probe. The determining the transition zone comprises determining the transition zone based on a noise image and the TGC matrix.

The one or more processors may be configured to determine the transition zone using an artificial intelligence (AI) model.

The transition zone may be substantially horizontal.

The transition zone may include a geometric shape.

The one or more processors may further be configured to determine another transition zone. The generating the blended image may include generating the blended image based on the transition zone and the other transition zone.

In another aspect, a method may include controlling an ultrasound probe to acquire a fundamental image of a region of interest of a subject; controlling the ultrasound probe to acquire a harmonic image of the region of interest of the subject; determining a transition zone at which to blend the harmonic image and the fundamental image; generating a blended image including harmonic image data from the harmonic image and fundamental image data from the fundamental image based on determining the transition zone; and controlling a display to display the blended image.

The method may include generating a noise image may be based on noise image data acquired by the ultrasound probe. The determining the transition zone may include determining the transition zone based on the noise image.

The method may include generating a time gain compensation (TGC) matrix based on TGC data acquired by the ultrasound probe. The determining the transition zone may include determining the transition zone based on a noise image and the TGC matrix.

The determining the transition zone may include using an artificial intelligence (AI) model.

The transition zone may be substantially horizontal.

The transition zone may include a geometric shape.

The method may include determining another transition zone. The generating the blended image may include generating the blended image based on the transition zone and the other transition zone.

In yet another aspect, a non-transitory computer-readable medium may store instructions that, when executed by one or more processors of an ultrasound imaging system, cause the one or more processors to: control an ultrasound probe to acquire a fundamental image of a region of interest of a subject; control the ultrasound probe to acquire a harmonic image of the region of interest of the subject; determine a transition zone at which to blend the harmonic image and the fundamental image; generate a blended image including harmonic image data from the harmonic image and fundamental image data from the fundamental image based on determining the transition zone; and control a display to display the blended image.

The one or more processors may further be configured to generate a noise image based on noise image data acquired by the ultrasound probe. The determining the transition zone may include determining the transition zone based on the noise image.

The one or more processors may further be configured to generate a time gain compensation (TGC) matrix based on TGC data acquired by the ultrasound probe. The determining the transition zone comprises determining the transition zone based on a noise image and the TGC matrix.

The one or more processors may be configured to determine the transition zone using an artificial intelligence (AI) model.

The transition zone may be substantially horizontal.

The transition zone may include a geometric shape.

The one or more processors may further be configured to determine another transition zone. The generating the blended image may include generating the blended image based on the transition zone and the other transition zone.

BRIEF DESCRIPTION OF DRAWINGS

FIG. 2 is a flowchart of an example process for generating a blended image including harmonic image data from the harmonic image and fundamental image data from the fundamental image based on determining a transition zone.

DETAILED DESCRIPTION

Figure 1:
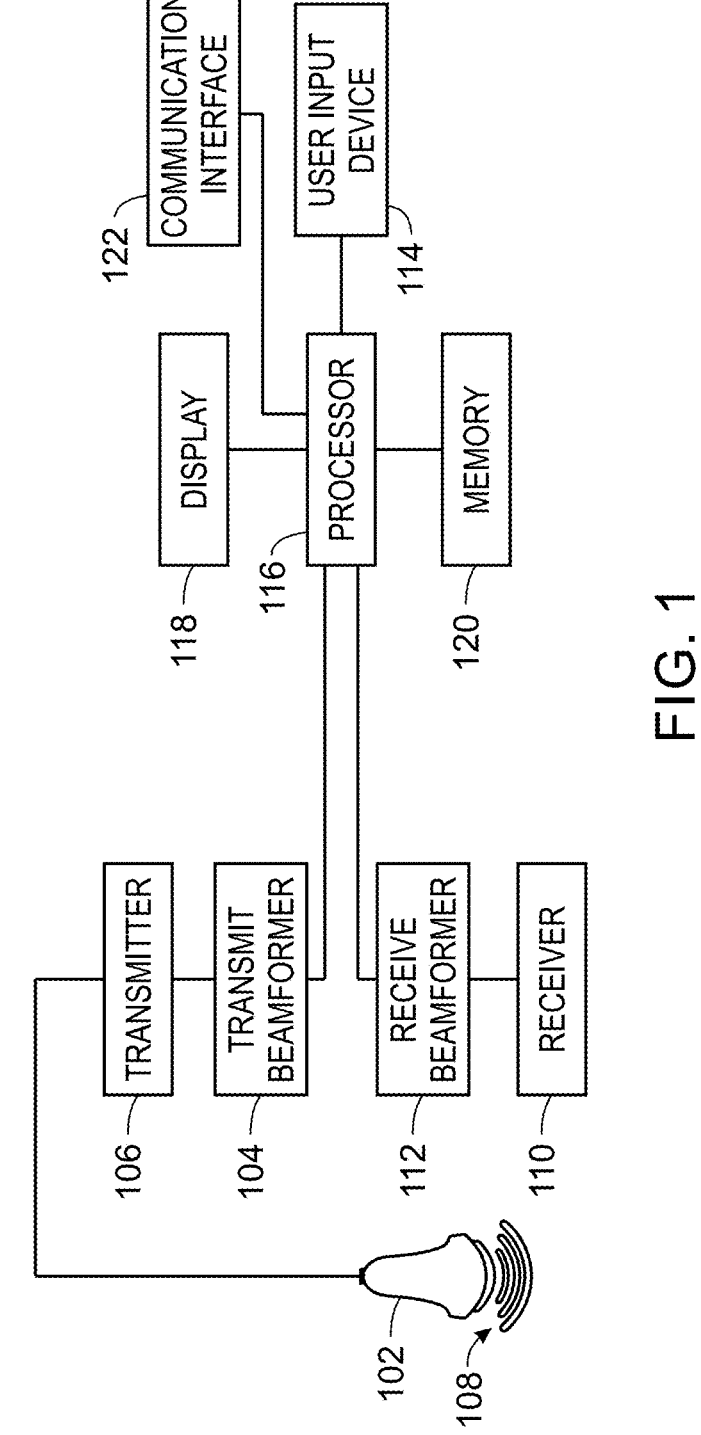
FIG. 1 is a diagram of an example ultrasound imaging system for generating a blended image including harmonic image data from the harmonic image and fundamental image data from the fundamental image based on determining a transition zone.

As addressed above, an ultrasound imaging system may acquire a harmonic image of a region of interest and a fundamental image of the region of interest. The harmonic image and the fundamental image may each have respective advantages and disadvantages. In other words, the harmonic image might have particular areas of increased resolution, increased signal to noise ratio, etc., and the fundamental image might also have particular areas of increased resolution, increased signal to noise ratio, etc. To exploit these relative advantages, an ultrasound imaging system may simultaneously display both the harmonic image and the fundamental image. In this case, the simultaneous display may occupy a significant portion of a display screen. Further, an operator might find the simultaneous display to be non-intuitive because the simultaneous display requires the operator to shift his or her attention between the harmonic image and the fundamental image. The non-intuitiveness of this display might be exacerbated during interventional procedures.

In other cases, an ultrasound imaging system may generate a blended image including harmonic image data from a harmonic image and fundamental image data from a fundamental image. The ultrasound imaging system may be configured with one or more predetermined depths at which to switch the display between the harmonic image data and the fundamental image data. In these cases, the generated blended image might appear artificial because the switch from the harmonic image data to the fundamental image data may be highly noticeable. Moreover, in these cases, the generated blended image might not capture advantageous portions of the harmonic image and the fundamental image. For instance, the blended image may include harmonic image data proximal of a predetermined depth and may include fundamental image data distal to the predetermined depth. However, the harmonic image may include an area that is of higher quality than the fundamental image distal to the predetermined depth, and/or the fundamental image may include an area that is of higher quality than the harmonic image proximal to the predetermined depth. In these cases, the blended image might not include these respective areas of higher quality because the predetermined depth is selected and utilized as an arbitrary switching point of the harmonic image data and the fundamental image data.

Some implementations herein provide an ultrasound imaging system for generating a blended image including harmonic image data from a harmonic image and fundamental image data from a fundamental image based on determining a transition zone. The ultrasound imaging system may control an ultrasound probe to acquire a fundamental image of a region of interest of a subject, and control the ultrasound probe to acquire a harmonic image of the region of interest of the subject. The ultrasound imaging system may generate a blended image including harmonic image data from the harmonic image and fundamental image data from the fundamental image based on determining the transition zone, and control a display to display the blended image. The blended image may include improved quality by including high quality areas of the harmonic image and high quality areas of the fundamental image based on the determined transition zone. Further, the blended image may include an improved and more realistic appearance over situations in which a predetermined transition zone is utilized. In this way, some implementations herein provide a technical improvement in the technical field of ultrasound image, and provide a technical improvement to ultrasound images by generating a blended image that utilizes a determined transition zone.

FIG. 1 is a diagram of an example ultrasound imaging system 100 for generating a blended image including harmonic image data from the harmonic image and fundamental image data from the fundamental image based on determining a transition zone. As shown in FIG. 1, the ultrasound imaging system 100 may include an ultrasound probe 102, a transmit beamformer 104, a transmitter 106, elements 108, a receiver 110, a receive beamformer 112, a user input device 114, a processor 116, a display 118, a memory 120, and a communication interface 122. The foregoing components may be connected via wired or wireless connections.

The ultrasound probe 102 may be configured to acquire ultrasound data. For example, the ultrasound probe 102 may be a linear probe, a phase array probe, a curved linear probe coupled with a position tracking system, a mechanically steered linear array transducer, a phased array transducer, a curved linear array transducer, an electronically steered 2D transducer array, an electronic 3D (e3D) probe, an electronic 4d (e4D) probe, a low profile wearable patch version of any of the foregoing probes, or the like. The ultrasound probe 102 may be configured to generate ultrasound signals, transmit the ultrasound signals towards a region of interest of a subject, receive echo ultrasound signals that are back-scattered from the region of interest of the subject, generate ultrasound data based on the echo ultrasound signals, and output the ultrasound data. The ultrasound probe 102 may be configured to transmit ultrasound signals having a fundamental frequency, and receive echo signals having the fundamental frequency and harmonic frequencies of the fundamental frequency. The fundamental frequency may be 2 MHz, 3 MHz, 4 MHz, or the like. The harmonic frequencies may include integer multiples of the fundamental frequency, or the like.

The transmit beamformer 104 may be configured to apply delay times to electrical signals provided to the elements 108 to focus corresponding ultrasound signals at a target location of the region of interest. The transmitter 106 may be configured to transmit electrical signals to the elements 108 to drive the elements 108 to emit ultrasound signals towards the target location. The elements 108 may be configured to receive the electrical signals from the transmitter 106, convert the electrical signals into ultrasound signals, and emit the ultrasound signals towards the target location. The elements 108 may be configured to receive echo ultrasound signals that are back-scattered by the target location, convert the echo ultrasound signals into electrical signals, and provide the electrical signals to the receiver 110. The receiver 110 may be configured to receive electrical signals from the elements 108, and provide the electrical signals to the receive beamformer 112. The receive beamformer 112 may apply delay times to the electrical signals received from the elements 108.

The user input device 114 may be configured to receive a user input, and provide the user input to the processor 116. For example, the user input device 114 may be a touch screen display, a keyboard, a keypad, a mouse, a button, a switch, a microphone, or the like. Additionally, or alternatively, the user input device 114 may be configured to sense information. For example, the user input device 114 may sense information from an electro-magnetic positioning system, an inertial measurement system, an accelerometer, a gyroscope, an actuator, or the like.

The processor 116 may be configured to perform the operations as described herein. For example, the processor 116 may be a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or the like. The processor 116 may be implemented in hardware, firmware, or a combination of hardware and software. The processor 116 may include one or more processors 116 configured to perform the operations described herein. For example, a single processor 116 may be configured to perform all of the operations described herein. Alternatively, multiple processors 116, collectively, may be configured to perform all of the operations described herein, and each of the multiple processors 116 may be configured to perform a subset of the operations described herein. For example, a first processor 116 may perform a first subset of the operations described herein, a second processor 116 may be configured to perform a second subset of the operations described herein, etc.

The processor 116 may be configured to control the ultrasound probe 102 to acquire ultrasound data. The processor 116 may be configured to control which of the elements 108 are active, and control the shape of a beam emitted from the ultrasound probe 102. The processor 116 may generate ultrasound images for display. For example, the processor 116 may generate B-mode images, color Doppler images, M-mode images, color M-mode images, or the like. The processor 116 may generate a fundamental image using echo signals having a fundamental frequency corresponding to the fundamental frequency of a transmitted ultrasound signal. The processor 116 may generate a harmonic image using echo signals having harmonic frequencies of a fundamental frequency corresponding to the fundamental frequency of a transmitted ultrasound signal. The processor 116 may determine a transition zone at which to blend the harmonic image and the fundamental image, and generate a blended image including harmonic image data from the harmonic image and fundamental image data from the fundamental image based on determining the transition zone. The processor 116 may control the display 118 to display the blended image The display 118 may be configured to display information. For example, the display 118 may be a monitor, a light-emitting diode (LED) display, a cathode ray tube, a projector display, a touchscreen, tablet computer, mobile phone, or the like. The display 118 may display the blended image including harmonic image data from the harmonic image and fundamental image data from the fundamental image.

The memory 120 may be configured to store information and/or instructions for use by the processor 116. The memory 120 may be a non-transitory computer-readable medium. For example, the memory 120 may be a random access memory (RAM), a read only memory (ROM), a flash memory, a magnetic memory, an optical memory, or the like. The memory 120 may be configured to store instructions that, when executed by the processor 116, cause the processor 116 to perform the operations described herein.

The communication interface 122 may be configured to enable the processor 116 to communicate with other devices, such as via a wired connection, a wireless connection, or a combination of wired and wireless connections. For example, the communication interface 122 may include an Ethernet interface, an optical interface, a coaxial interface, an infrared interface, a radio frequency (RF) interface, a universal serial bus (USB) interface, a wireless fidelity (Wi-Fi) interface, a cellular network interface, or the like.

The number and arrangement of the components of the ultrasound imaging system 100 shown in FIG. 1 are provided as an example. In practice, the ultrasound imaging system 100 may include additional components, fewer components, different components, or differently arranged components than those shown in FIG. 1. Additionally, or alternatively, a set of components (e.g., one or more components) of the ultrasound imaging system 100 may perform one or more functions described as being performed by another set of components of the ultrasound imaging system 100.

FIG. 2 is a flowchart of an example process 200 for generating a blended image including harmonic image data from the harmonic image and fundamental image data from the fundamental image based on determining a transition zone.

As shown in FIG. 2, the process 200 may include controlling an ultrasound probe to acquire a fundamental image of a region of interest of a subject (operation 210). For example, the processor 116 may control the ultrasound probe 102 to acquire a fundamental image of a region of interest of a subject. The ultrasound imaging system 100 may acquire the fundamental image using a fundamental imaging technique. For example, the ultrasound imaging system 100 may transmit ultrasound signals using a spectral band including a fundamental frequency, receive echo signals having the fundamental frequency, and acquire a fundamental image using the echo signals having the fundamental frequency. The fundamental frequency may be 2 MHz, 3 MHz, 4 MHz, etc. The region of interest may be any anatomical region of the subject. For example, the region of interest may be the heart, the pancreas, the liver, a blood vessel, or the like. The subject may be a patient, an animal, a phantom, or the like.

As further shown in FIG. 2, the process 200 may include controlling the ultrasound probe to acquire a harmonic image of the region of interest of the subject (operation 220). For example, the processor 116 may control the ultrasound probe 102 to acquire a harmonic image of the region of interest of the subject. The ultrasound imaging system 100 may acquire the harmonic image using a harmonic imaging technique (e.g., tissue harmonic imaging, pulse inversion imaging, superharmonic imaging, or the like). For example, the ultrasound imaging system 100 may transmit ultrasound signals using a spectral band including a fundamental frequency, receive echo signals having harmonic frequencies of the fundamental frequency, and acquire a harmonic image using the echo signals having the harmonic frequencies of the fundamental frequency. The harmonic frequencies may be integer multiples of the fundamental frequency. For example, if the fundamental frequency is 3 MHZ, then the second harmonic frequency may be 6 MHz, the third harmonic frequency may be 9 MHZ, etc.

As further shown in FIG. 2, the process 200 may include determining a transition zone at which to blend the harmonic image and the fundamental image (operation 230). For example, the processor 116 may determine a transition zone at which to blend the harmonic image and the fundamental image.

The transition zone may refer to a region of an image at which to transition from the harmonic image to the fundamental image, or to transition from the fundamental image to the harmonic image. The transition zone may include any geometrical shape, such as the geometrical shapes shown in FIGS. 7A-7E. For example, the transition zone may be a straight line, a curved line, a rectangle, a square, a circle, a triangle, or the like. The geometrical shape of the transition zone may define the respective locations of the harmonic image data and the fundamental image data in the blended image. For example, if the transition zone is a line, then a region that is proximal to the transition zone may include harmonic image data, and a region that is distal to the transition zone may include fundamental image data, or vice versa. Alternatively, and as an example, if the transition zone is an enclosed shape, then the region internal to transition zone may include fundamental image data, and the region external to the transition zone may include harmonic image data, or vice versa. The blended image may include any number of transition zones (e.g., a single transition zone, two transition zones, etc.).

According to an embodiment, the processor 116 may determine the transition zone based on a noise image, as described in more detail in connection with FIG. 4. For example, the processor 116 may control the ultrasound probe 102 to acquire noise image data, generate a noise image based on the noise image data, and determine the transition zone at which to blend the harmonic image and the fundamental image based on the noise image.

According to an embodiment, the processor 116 may determine the transition zone based on a noise image and a TGC matrix, as described in more detail in connection with FIG. 5. For example, the processor 116 may control the ultrasound probe 102 to acquire TGC data, generate a TGC matrix based on the TGC data, and determine the transition zone at which to blend the harmonic image and the fundamental image based on the TGC data.

According to an embodiment, the processor 116 may determine the transition zone based on an output from an artificial intelligence (AI) model. For example, the processor 116 may input the harmonic image and/or the fundamental image into an AI model, may receive an output of the AI model, and determine the transition zone at which to blend the harmonic image and the fundamental image based on the output of the AI model. In this case, the AI model may be trained to receive a harmonic image and/or a fundamental image, and determine a transition zone based on the harmonic image and/or the fundamental image. For example, the AI model may be trained using training data that identifies areas of low quality and/or areas of high quality. Alternatively, as an example, the AI model may be trained using training data that identifies areas of a fundamental image that are of higher quality than a corresponding harmonic image, or vice versa.

As further shown in FIG. 2, the process 200 may include generating a blended image including harmonic image data from the harmonic image and fundamental image data from the fundamental image based on determining the transition zone (operation 240). For example, the processor 116 may generate a blended image including harmonic image data from the harmonic image and fundamental image data from the fundamental image based on determining the transition zone.

The processor 116 may generate the blended image using the transition zone. For example, the processor 116 may generate the blended image such that the harmonic image data is positioned at a first position relative to the transition zone, and the fundamental image data is positioned at a second location relative to the transition zone. For example, if the transition zone is a line, then a region that is proximal to the transition zone may include harmonic image data, and a region that is distal to the transition zone may include fundamental image data, or vice versa. Alternatively, and as an example, if the transition zone is an enclosed shape, then the region internal to transition zone may include fundamental image data, and the region external to the transition zone may include harmonic image data, or vice versa.

According to an embodiment, the processor 116 may generate the blended image using an image blending technique. For example, the processor 116 may generate the blended image using linear blending, Gaussian blending, Laplacian blending, Poisson blending, or the like. According to an embodiment, the processor 116 may use blend weights to generate the blended image. For example, the blend weights may identify a ratio of the fundamental image data to the harmonic image data at various depths of the image, or vice versa. According to an embodiment, the processor 116 may generate the blended image by transitioning entirely from the harmonic image to the fundamental image at a particular region defined by the transition zone, or vice versa. For example, the blended image may include the harmonic image data proximal to the particular region and the fundamental image data distal to the particular region. In other words, the harmonic image data and the fundamental image data might not be blended in some cases.

As further shown in FIG. 2, the process 200 may include controlling a display to display the blended image (operation 250). For example, the processor 116 may control the display 118 to display the blended image.

The blended image may be a single image that includes harmonic image data from a harmonic image and fundamental image data from a fundamental image. The blended image may be of higher quality than the harmonic image and the fundamental image, respectively, because the blended image uses constituent parts of the harmonic image that are of higher quality than the fundamental image, and vice versa. In this way, the embodiments herein provide a technical improvement to medical imaging by reducing the number of images that are displayed on a display screen as compared to situations where a fundamental image and a harmonic image are both concurrently displayed, and by improving the displayed image by using respective portions of the fundamental image and the harmonic image that are of higher quality as compared to each other.

Although FIG. 2 depicts particular operations and a particular sequence of operations, it should be understood that the process 200 may include other operations, or differently arranged operations, in other embodiments.

Figure 3A:
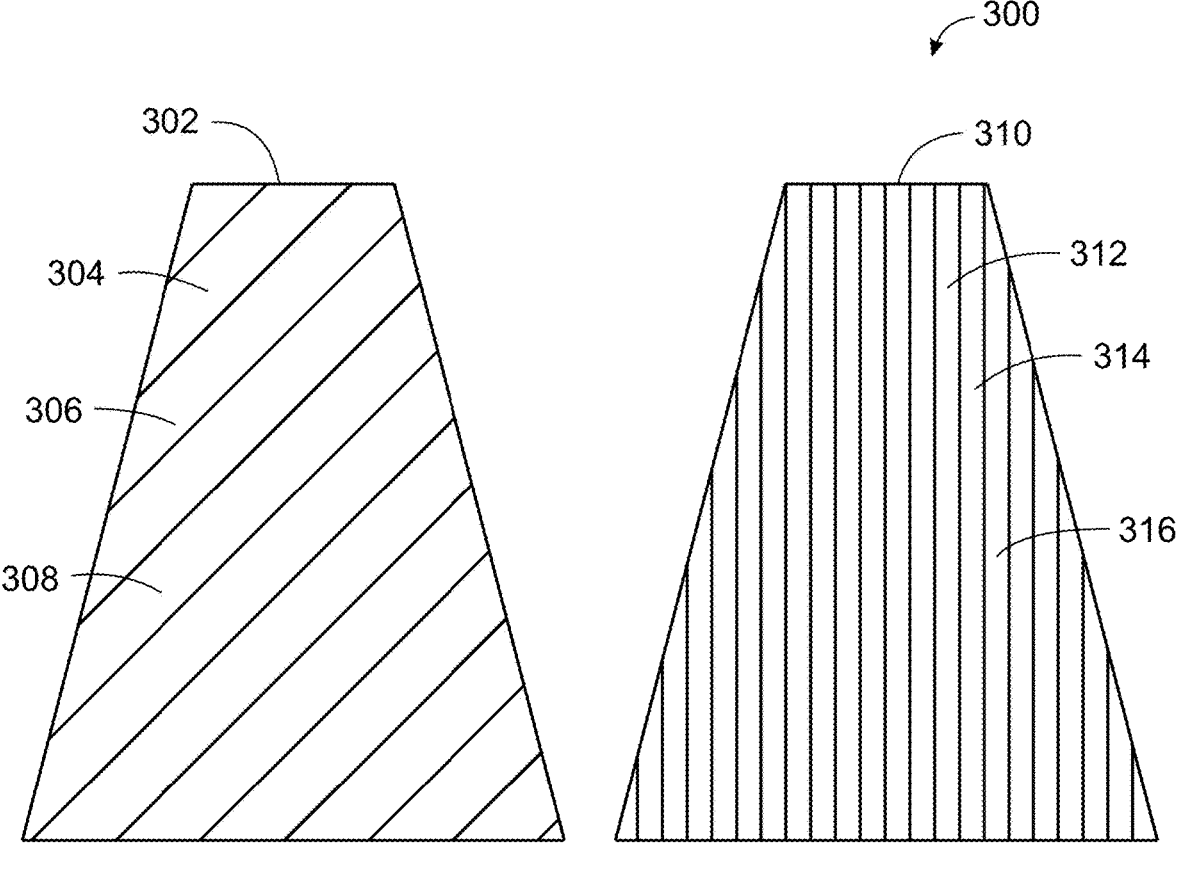
FIG. 3A is a diagram of an example fundamental image and an example harmonic image.

FIG. 3A is a diagram 300 of an example fundamental image and an example harmonic image. As shown in FIG. 3A, the ultrasound imaging system 100 may acquire a fundamental image 302 having a first region 304, a second region 306, and a third region 308. Further, the ultrasound imaging system 100 may acquire a harmonic image 310 having a first region 312, a second region 314, and a third region 316. The first region 304 of the fundamental image may be generally of lower quality than the first region 312 of the harmonic image. The second region 306 of the fundamental image may be generally of higher quality in some areas than as compared to the second region 314 of the harmonic image, and generally of lower quality in other areas than as compared to the second region 314 of the harmonic image. The third region 308 of the fundamental image may of generally higher quality than the third region 316 of the harmonic image.

Figure 3B:
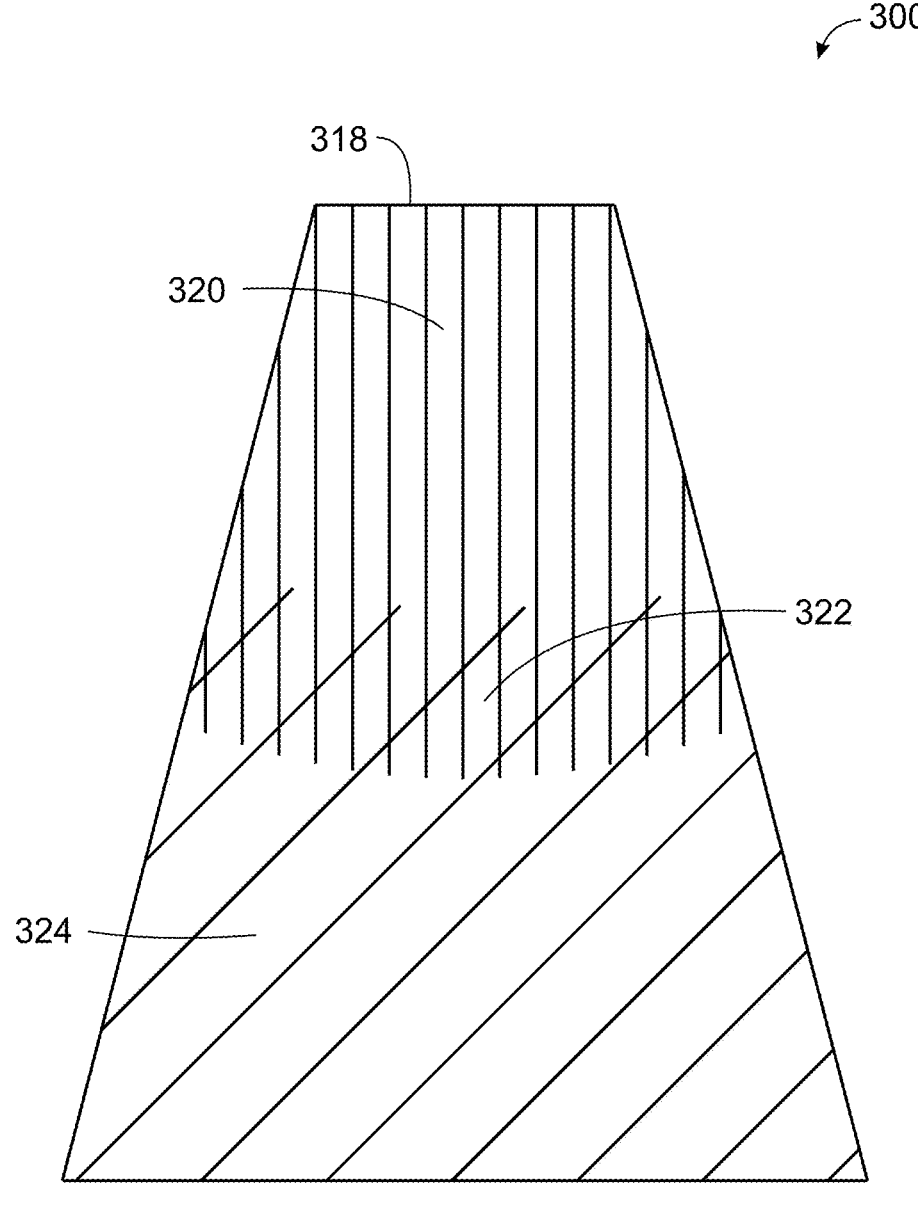
FIG. 3B is a diagram of an example blended image including harmonic image data from the harmonic image of FIG. 3A and fundamental image data from the fundamental image of FIG. 3A.

FIG. 3B is a diagram 300 of an example blended image including harmonic image data from the harmonic image of FIG. 3A and fundamental image data from the fundamental image of FIG. 3A. As shown in FIG. 3B, the ultrasound imaging system 100 may generate a blended image 318 using harmonic imaging data from the harmonic image 310 of FIG. 3A and using fundamental imaging data from the fundamental image 302 of FIG. 3A. The blended image 318 may include a first region 320 that includes the harmonic image data from the first region 312 of the harmonic image 310, a second region 322 that includes the harmonic image data from the second region 314 of the harmonic image 310 and the fundamental image data from the second region 306 of the fundamental image 302, and a third region that includes the fundamental image data from the third region 308 of the fundamental image 302. The transition zone (or zones) may identify how the various regions are delineated.

Figure 4:
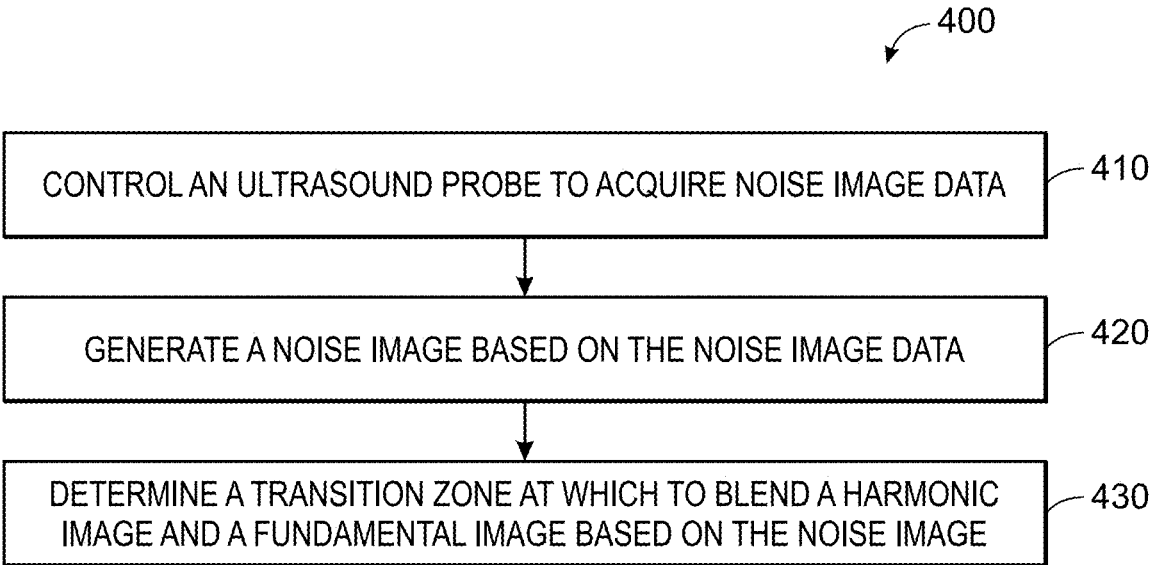
FIG. 4 is a flowchart of an example process for generating a noise image and determining a transition zone based on the noise image.

FIG. 4 is a flowchart of an example process 400 for generating a noise image and determining a transition zone based on the noise image. The noise image may be an image acquired with turned-off transmitters 106 but with a preselected time gain compensation pattern of the acquired signal. The signal magnitude that is acquired with turned off transmitters 106 is equal to the magnitude of the received signal in the middle of a big fluid collection with turned-on transmitters 106 and the same time gain compensation pattern. The processor 116 is configured to compute a binary mask indicating the areas for which the noise signal has a magnitude that is smaller than or equal to (1) or larger than (0) a predetermined threshold. The example process 400 may be activated in harmonic mode, and the process 400 may also be activated in fundamental mode. In this way, the processor 116 may generate a harmonic noise image and/or a fundamental noise image.

As shown in FIG. 4, the process 400 may include controlling an ultrasound probe to acquire noise image data (operation 410). For example, the processor 116 may control the ultrasound probe 102 to receive echo signals to acquire noise image data. If the processor 116 is operating in harmonic mode, then the noise image data may be harmonic noise image data. Alternatively, if the processor 116 is operating in fundamental mode, then the noise image data may be fundamental noise image data. The echo signals may be ultrasound signals that were generated by the region of interest in response to the ultrasound probe 102 being in proximity to the region of interest, and without the transmission of an ultrasound signal by the ultrasound probe 102. The echo signals may be indicative of electrical noise of the transducer of the ultrasound probe 102, and a dependency of the electrical noise per depth. In other words, the acquisition of the echo signals associated with the noise image data may be performed without having transmitted ultrasound signals to the region of interest. Put yet another way, the acquisition of the echo signals is not in response to a transmission of the ultrasound probe 102. The noise image data may be one or more lines of an image. The noise image data may provide a measurement of an amplitude of noise as a function of depth. The processor 116 may controlling the ultrasound probe 102 to receive noise signals for a predetermined time duration before transmitting ultrasound signals, and acquire the noise image data based on the noise image signals.

As further shown in FIG. 4, the process 400 may include generating a noise image based on the noise image data (operation 420). For example, the processor 116 may generate a noise image based on the noise image data. If the processor 116 is operating in harmonic mode, then the noise image may be a harmonic noise image. Alternatively, if the processor 116 is operating in fundamental mode, then the noise image may be a fundamental noise image. The processor 116 may generate the noise image by expanding the one or more lines of the noise image data. The processor 116 may generate a noise image by expanding the one or more lines corresponding to noise to a full number of lines for the blended image (or the fundamental image or the harmonic image). To do so, the processor 116 may determine an average of the one or more lines to form an average line and copy the typical line for the full number of lines. Alternatively, the processor 116 may smooth the typical line using a one-dimensional finite impulse response (FIR) or infinite impulse response (IIR) filter prior to copying the one or more lines. The noise image provides a measurement of an amplitude of the noise as a function of depth.

As further shown in FIG. 4, the process 400 may include determining a transition zone at which to blend a harmonic image and a fundamental image based on the noise image (operation 430). For example, the processor 116 may determine a transition zone at which to blend a harmonic image and a fundamental image based on the noise image.

According to an embodiment, the processor 116 may use the noise image by averaging lines of the noise image, and thereby determining the noise level as a smooth function of depth. The processor 116 may multiply the noise level (before log compression) with the applied gain for the live image divided by the gain applied during noise recording to establish the current noise level as a function of depth. To avoid visible noise in a fluid collection, the processor 116 may determine the depth at which the noise exceeds a pre-defined threshold for the allowed visible noise in a fluid collection. The depth may correspond to the transition zone. For example, the depth may be where the transition from the harmonic image to the fundamental image takes place. In order to avoid a visible transition, the processor 116 may blend the harmonic image and the fundamental image over the transition zone. The transition zone may include a width including a fixed number of samples (e.g., 10 samples), a fixed number of millimeters, or the like.

According to an embodiment, the processor 116 may analyze the values of the noise image to determine the transition zone. For example, the processor 116 may determine that one or more values of the noise image satisfy a threshold, and determine the transition zone based on the position of the one or more values of the noise image. Alternatively, the processor 116 may detect a region of the noise image that satisfies a predetermined pattern, and determine the transition zone based on the position of the one or more values of the noise image.

Figure 5:
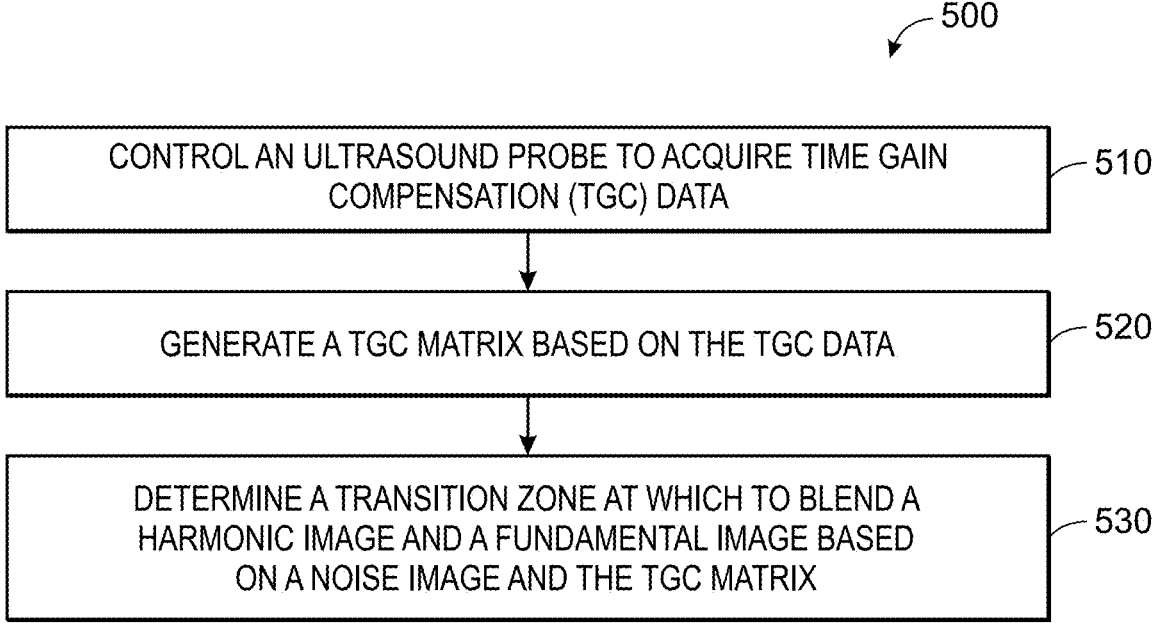
FIG. 5 is a flowchart of an example process for generating a TGC matrix and determining a transition zone based on the noise image and the TGC matrix.

FIG. 5 is a flowchart of an example process 500 for generating a noise image and a time gain compensation (TGC) matrix, and determining a transition zone based on the noise image and the TGC matrix. The noise image may be similar to the noise image generated with respect to the process 400 as described above in connection with FIG. 4. The TGC matrix may be a matrix that has the same size as the current live image which is generated by the use of an initial specific time gain compensation pattern. After being computed, the TGC matrix may be used as an element-wise pixel-by-pixel multiplication factor of the current image before log-compression to produce the final gain-compensated image before log-compression. The processor 116 may multiply element-wise the TGC matrix by the noise image (e.g., the fundamental noise image or the harmonic noise image), and compute a binary mask indicating the areas for which the noise signal has a magnitude that is smaller than or equal to (1) or larger than (0) a predetermined threshold. The process 500 may be activated in harmonic mode, and the process may also be activated in fundamental mode. In this way, the process 500 may use a harmonic noise image and/or a fundamental noise image. After blending of the harmonic image and the fundamental image, the TGC matrix may be recalculated.

As shown in FIG. 5, the process 500 may include controlling an ultrasound probe to acquire TGC data (operation 510). For example, the processor 116 may control the ultrasound probe 102 to acquire TGC data. The TGC data may be radiofrequency (RF) data, in-phase quadrature (IQ) data, down-sampled selected cross-correlation data, log-Data, normalization parameters, and/or down-sampled and uncompressed envelope data.

The ultrasound imaging system 100 may generate RF data. For example, ultrasound imaging system 100 may be configured to perform beamforming by delaying echo signals from each of the elements 108, summing the delayed signals, and generate the RF data.

The ultrasound imaging system 100 may generate IQ data based on the RF data. For example, the ultrasound imaging system 100 may be configured to convert the RF-data to the complex-value IQ domain, and generate the IQ data. The ultrasound imaging system 100 may multiply the RF signal by a complex sinusoid signal. The ultrasound imaging system 100 may process the IQ data, such as by low pass filtering, decimating, etc.

The ultrasound imaging system 100 may be configured to process the RF data and/or the IQ data. For example, the ultrasound imaging system 100 may use the IQ data for generating envelope data by computing the amplitude of the complex IQ signal for every sample in every scan line. In another example, the ultrasound imaging system 100 may filter the RF data with a filter, such as a finite impulse response (FIR), an infinite impulse response (IIR) filter, or the like. In this case, the ultrasound imaging system 100 may run the filtered RF data through an envelope detector. The ultrasound imaging system 100 may log compress the envelope data into a grayscale format, downscale the compressed data to reduce the load for subsequent processing, and/or otherwise process the data.

The ultrasound imaging system 100 may be configured to provide TGC. For example, the ultrasound imaging system 100 may perform fully automatic TGC, continuously adaptive TGC, and/or on-demand TGC. The ultrasound imaging system 100 may use axial TGC, axial-lateral TGC, axial-lateral-overall TGC, axial-overall TGC, or the like. The ultrasound imaging system 100 may receive the IQ data and the envelope data, perform TGC.

The ultrasound imaging system 100 may receive the IQ data and the envelope data. The ultrasound imaging system 100 may receive a frame of IQ and envelope data, and determines whether the TGC matrices are to be generated. According to an embodiment, TGC matrices are generated for every frame. Alternatively, TGC matrices are not computed every frame. For example, the ultrasound imaging system 100 may determine whether the TGC matrices are to be generated be based on frame rate, system load, a predetermined interval, a number frames compounded, a default or user setting, or the like. For example, the ultrasound imaging system 100 may generate the TGC matrices for every other frame, every n-th frame, or the like.

The ultrasound imaging system 100 may generate a cross-correlation between currently received IQ data and previously received IQ data. The ultrasound imaging system 100 may select a largest value, element-wise, from a set of the recently computed cross-correlation images. For example, where the set includes the three most recently computed cross-correlation images, the ultrasound imaging system 100 may select the cross-correlation images generated for the n-th and the (n−1) IQ data, the (n−1) and the (n−2) IQ data, and the (n−2) and the (n−3) IQ data.

The ultrasound imaging system 100 may down-sample the selected values, and down-sample the envelope data. The ultrasound imaging system 100 may normalize the down-sampled envelope data is normalized, and may generate logData. The ultrasound imaging system 100 may uncompress the normalized envelope data. The ultrasound imaging system 100 may filter the cross-correlation data. For example, the ultrasound imaging system 100 may filter the cross-correlation data with a 2D low-pass filter.

The ultrasound imaging system 100 may filter the envelope data. For example, the ultrasound imaging system 100 may pass the data through two independent processing chains, respectively, with a first 2D low-pass filter having a first size and a second 2D low-pass filter having a second size.

The ultrasound imaging system 100 may generate a mask to indicate the location of samples of soft tissue. The ultrasound imaging system 100 may exclude areas likely to contain fluid or noise. The ultrasound imaging system 100 may determine these areas using thresholding of the normalized log compressed image logData.

The ultrasound imaging system 100 may refine the mask of soft tissue areas. The ultrasound imaging system 100 may generate a final location or mask of trusted tissue samples. The excluded areas may be areas for which cross-correlation is very low or from tissue samples distal to large fluid collections. Cross-correlation is very low in regions of fluid, noise, or a mixture of tissue and fluid or noise.

The ultrasound imaging system 100 may determine median data of the trusted samples. The median data may be a scalar. The ultrasound imaging system 100 may exclude the regions of low cross-correlation (noise and non-dark fluid) from the masked data using the cross-correlation data. In this way, the output mask might not be binary, and instead may represent a fidelity metric indicating to what extent a particular sample is treated as a soft tissue sample. The fidelity for a sample is based on the magnitude of a local estimate of the cross-correlation relative to the average cross-correlation in the near-field. The fidelity for samples for which the local cross-correlation is less than half the near-field cross-correlation is set to zero.

The ultrasound imaging system 100 may exclude regions distal to large fluid collections. The ultrasound imaging system 100 may identify large fluid collections by low values in a low-pass filtered image of the relative cross-correlation. The ultrasound imaging system 100 may median filter the mask.

The ultrasound imaging system 100 may average the mask is averaged laterally, and generate a 1D array. The ultrasound imaging system 100 may select a minimum element-wise, from the laterally averaged data. The ultrasound imaging system 100 may filter the minimum with, as an example, a 1-D low pass filter.

The ultrasound imaging system 100 may blend every sample of the logData with the median data based on the associated fidelity of the sample. The ultrasound imaging system 100 may determine a regional weighted average or median using trusted sample. The ultrasound imaging system 100 may axially expand the region until a threshold number of trusted samples are within the region, which might result in a featureless, blended, and smoothed version of the logData.

The ultrasound imaging system 100 may average the blended and smoothed logData laterally, and generate a 1-D array or curve. The array or curve may express the average brightness of the soft tissue at each sample depth of the logData.

The ultrasound imaging system 100 may process the laterally averaged data using the normalizing parameters to convert from the normalized range back to the original range of the logarithmically compressed data. For example, the ultrasound imaging system 100 may multiply the scaled data with the original range, and add the original minimum value. The ultrasound imaging system 100 may smooth the output using a 1-D FIR filter.

As further shown in FIG. 5, the process 500 may include generating a TGC matrix based on the TGC data (operation 520). For example, the processor 116 may generate a TGC matrix based on the TGC data.

The ultrasound imaging system 100 may generate an axial TGC matrix based on the axially smoothed data. For example, the ultrasound imaging system 100 may generate a reciprocal curve, and then populate each scan line of the axial TGC matrix by the reciprocal curve.

The ultrasound imaging system 100 may blend the samples of logData with the median data based on the fidelity of the sample. The ultrasound imaging system 100 may determine a regional weighted average or median using trusted samples. The ultrasound imaging system 100 may expand a region laterally until a threshold number of trusted samples are within the region, which may result in an image that expresses the average brightness of the soft tissue for each scanline of logData at different coarsely quantized depths.

The ultrasound imaging system 100 may average the lateral image axially, such as along scanlines, and generate a 1-D array or curve expressing the average brightness of the soft tissue for each scanline of logData. The ultrasound imaging system 100 may smooth the output using a 1-D FIR filter.

The ultrasound imaging system 100 may determine the lateral TGC matrix based on the laterally smoothed data by populating the reciprocal curve of the output of to every row of the lateral TGC matrix.

As further shown in FIG. 5 the process 500 may include determining a transition zone at which to blend a harmonic image and a fundamental image based on a noise image and the TGC matrix (operation 530). For example, the processor 116 may determine a transition zone at which to blend a harmonic image and a fundamental image based on a noise image the TGC matrix.

According to an embodiment, the processor 116 may analyze the values of the TGC matrix to determine the transition zone. For example, the processor 116 may determine that one or more values of the TGC matrix satisfy a threshold, and determine the transition zone based on the position of the one or more values of the TGC matrix. Alternatively, the processor 116 may detect a region of the TGC matrix that satisfies a predetermined pattern, and determine the transition zone based on the position of the one or more values of the TGC matrix.

Figure 6A:
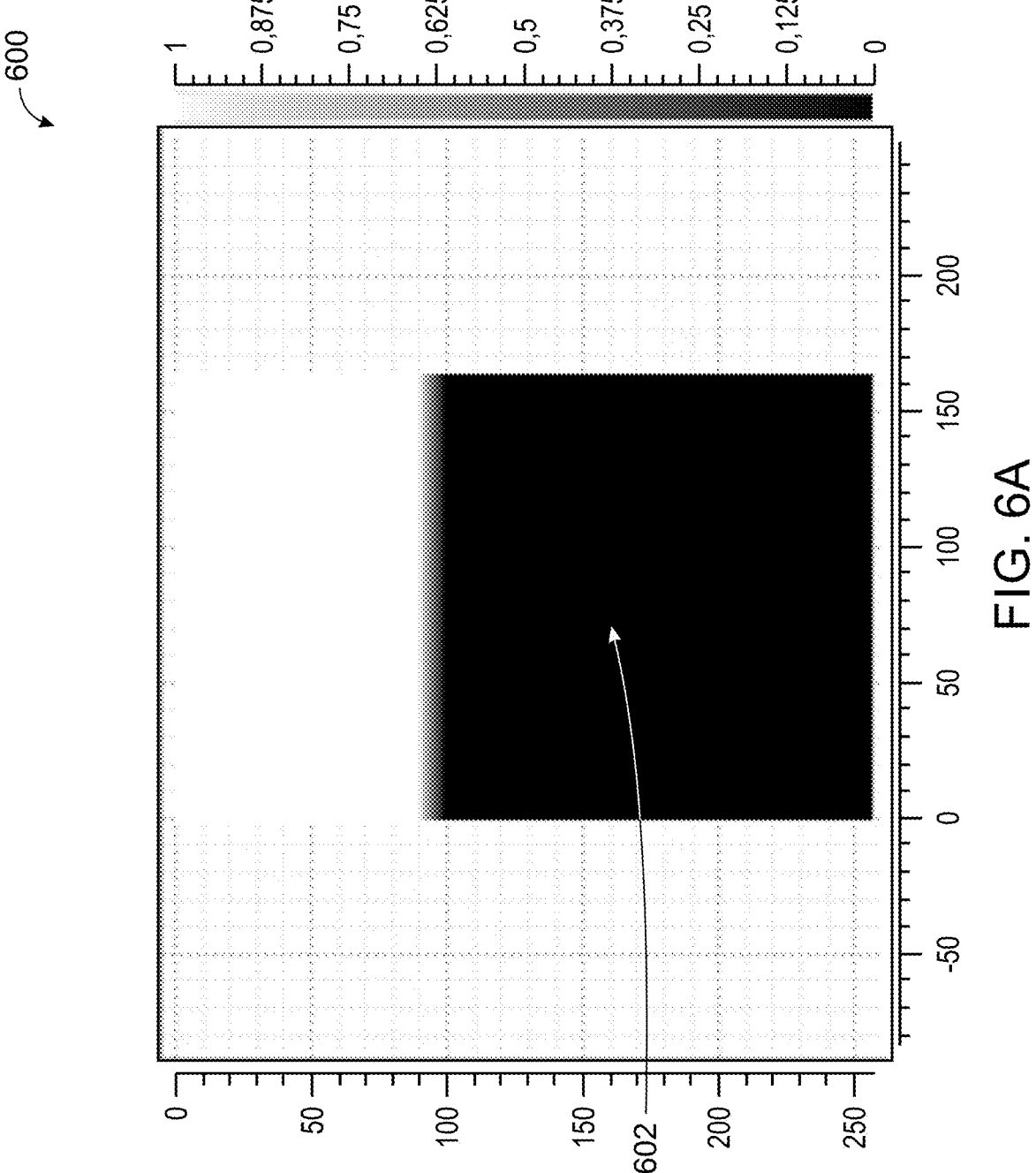
FIG. 6A is a diagram of example blend weights for generating a blended image.

FIG. 6A is a diagram 600 of example blend weights for generating a blended image. As shown in FIG. 6A, the ultrasound imaging system 100 may use blend weights 602 that identify a ratio of the fundamental image data to the harmonic image data at various depths of the image, or vice versa. For instance, the blend weights identify that the harmonic image data is to be used from pixels 0 through 90, that the harmonic image data and the fundamental image data are to be blended at pixels 90 through 100, and that the fundamental image data is to be used at pixels 100 through 250 of the blended image. The values of the blend weights identify the amount of blending of the fundamental image and the harmonic image.

Figure 6B:
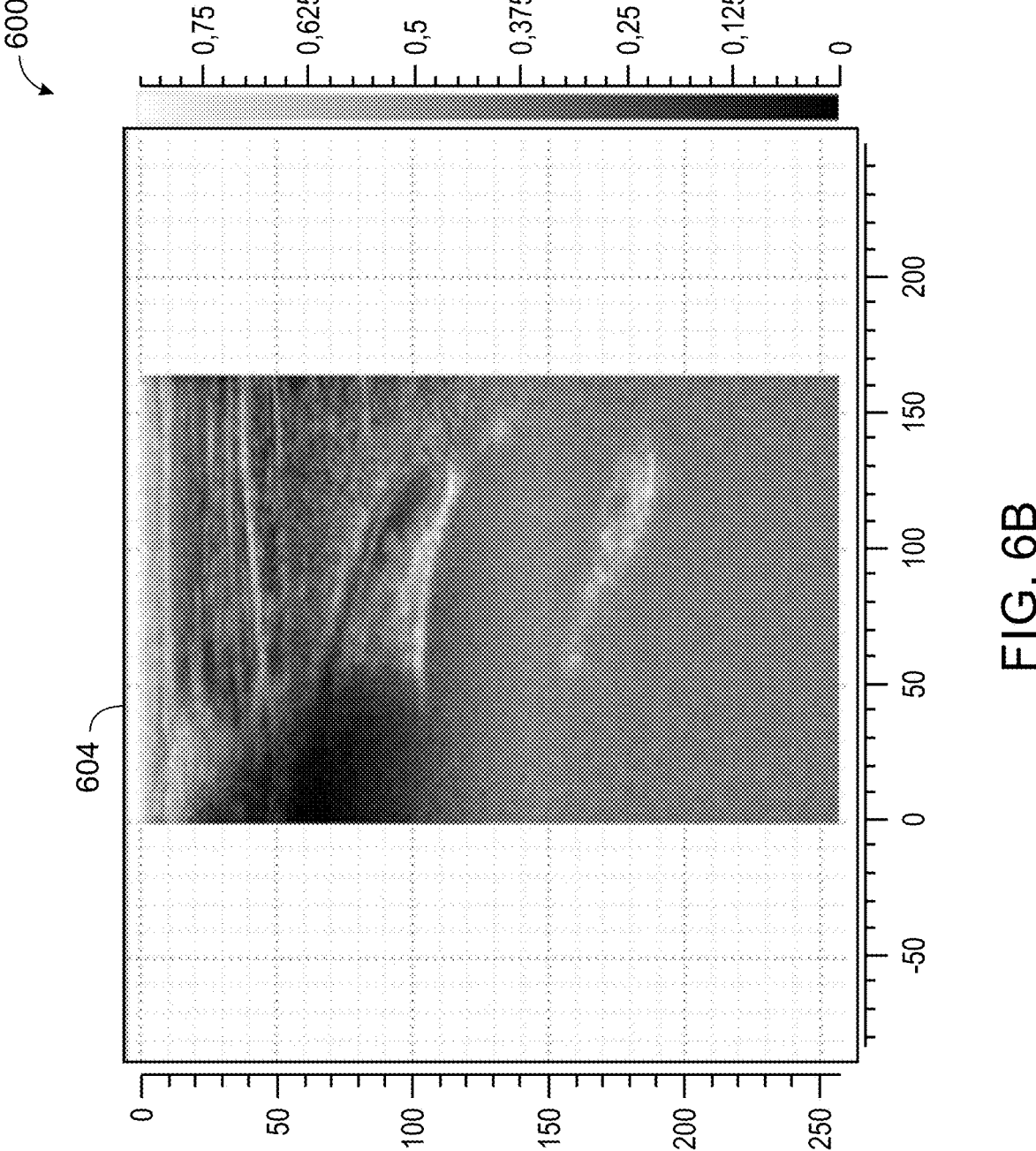
FIG. 6B is a diagram of an example harmonic image of a region of interest of a subject.

FIG. 6B is a diagram 600 of an example harmonic image of a region of interest of a subject. As shown in FIG. 6B, the ultrasound imaging system 100 may acquire a harmonic image 604. As shown, the harmonic image is of relatively high quality at pixels 0 through 100, and is of relatively low quality at pixels 100 through 250.

Figure 6C:
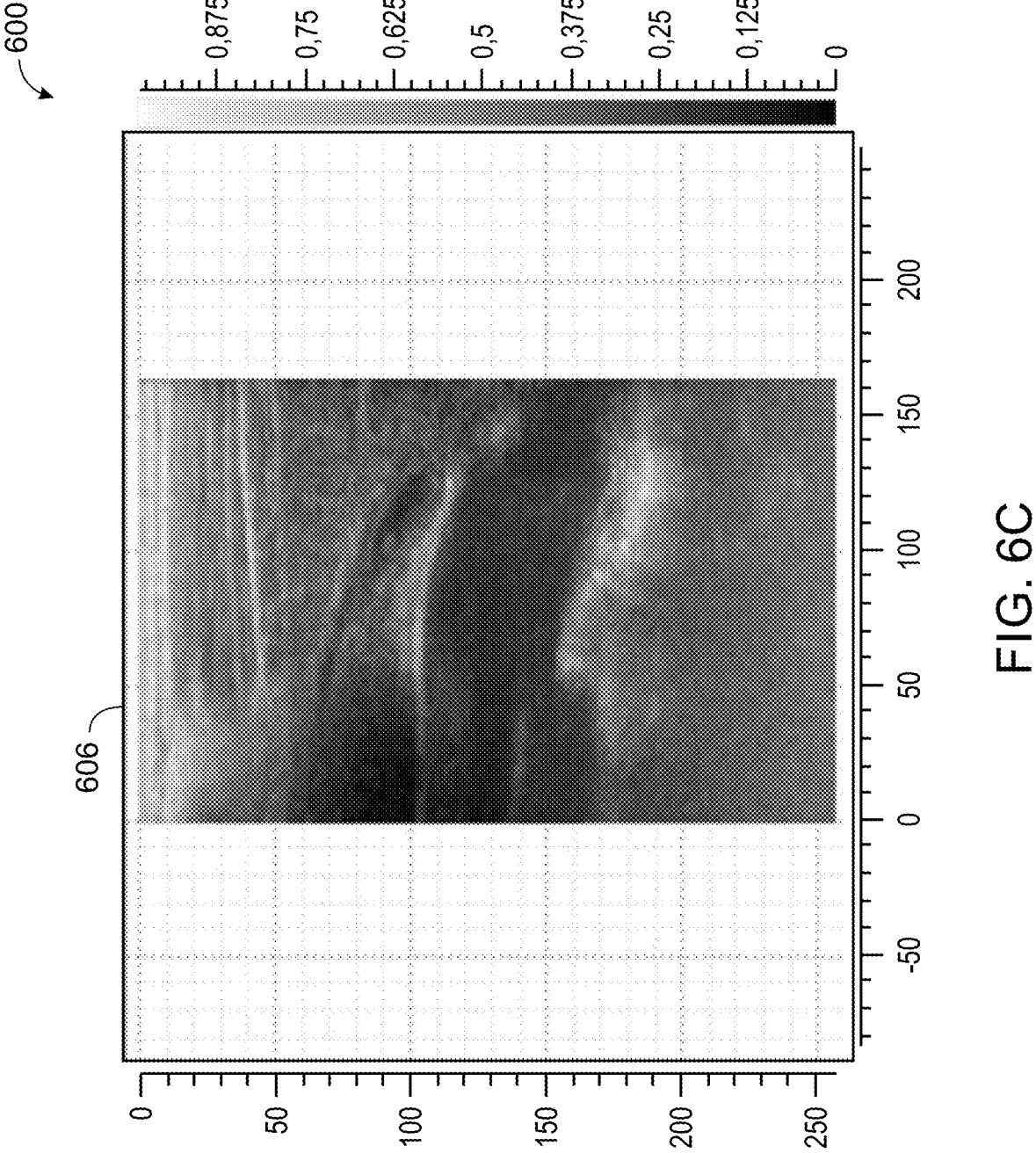
FIG. 6C is a diagram of an example fundamental image of the region of interest of the subject.

FIG. 6C is a diagram 600 of an example fundamental image of the region of interest of the subject. As shown in FIG. 6C, the ultrasound imaging system 100 may acquire a fundamental image 606. As shown, the fundamental image is of relatively lower quality than the harmonic image 604 at pixels 0 through 100, but is of relatively higher quality than the harmonic image 604 at pixels 100 through 250.

Figure 6D:
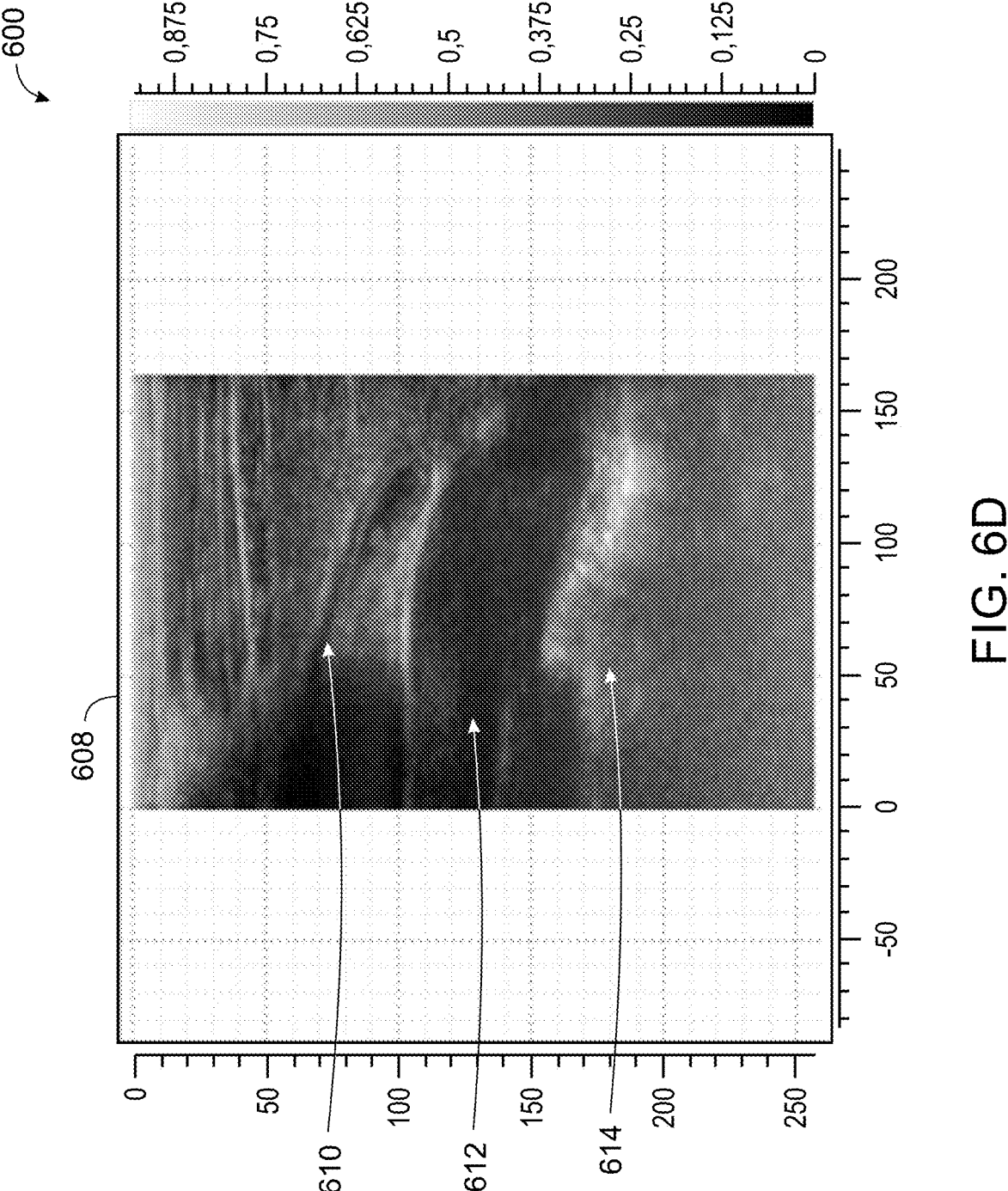
FIG. 6D is a diagram of an example blended image including harmonic image data from the harmonic image of FIG. 6B and fundamental image data from the fundamental image of FIG. 6C that is generated using the blend weights of FIG. 6A.

FIG. 6D is a diagram of an example blended image including harmonic image data from the harmonic image of FIG. 6B and fundamental image data from the fundamental image of FIG. 6C that is generated using the blend weights of FIG. 6A. As shown in FIG. 6D, the ultrasound imaging system 100 may generate a blended image 608 that includes a first region 610, a second region 612, and a third region 614. The second region 612 may include the transition zone. In this way, the first region 610 may include the harmonic image data of the harmonic image 604, the second region 612 may include a blend of the harmonic image data from the harmonic image 604 and fundamental image data of the fundamental image 606, and the third region 614 may include fundamental image data of the fundamental image 606.

Figure 7A:
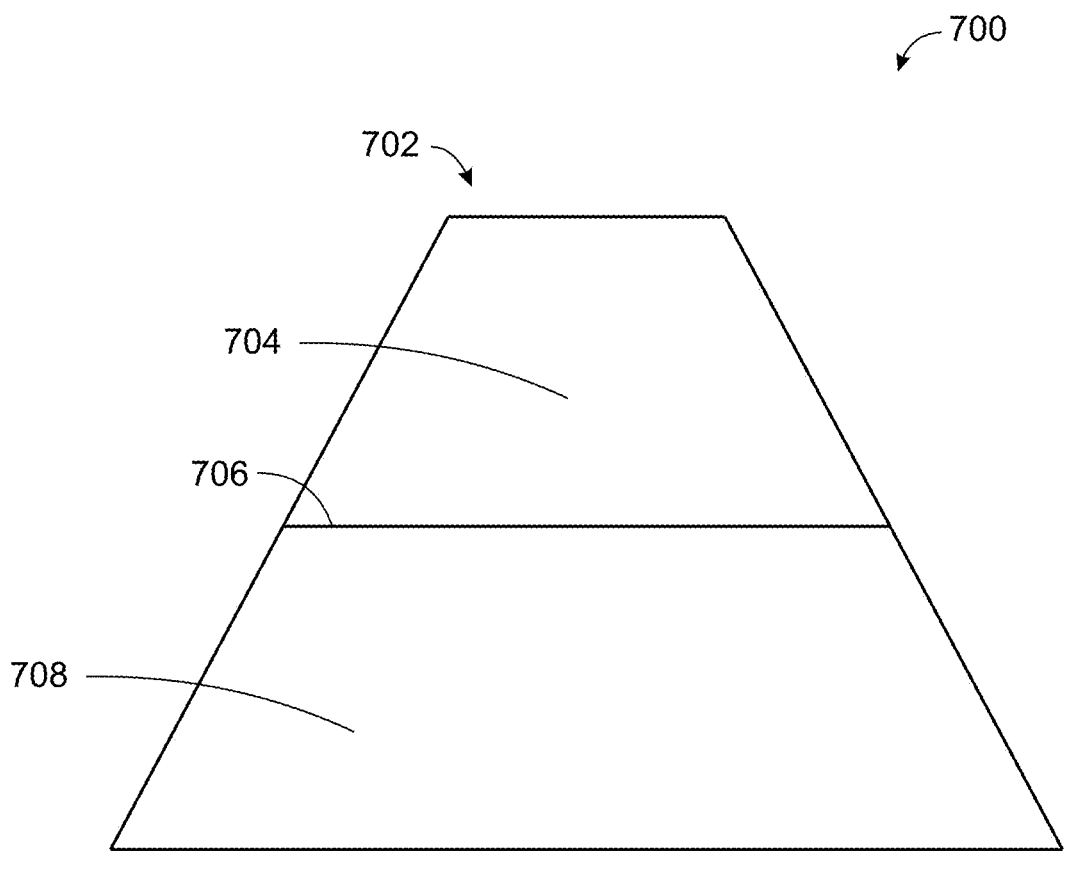
FIG. 7A is a diagram of an example transition zone in the form of a straight line.

FIG. 7A is a diagram 700 of an example transition zone in the form of a straight line. As shown in FIG. 7A, the blended image 702 may include a region 704 that includes harmonic image data (or fundamental image data), a transition zone 706 in the form of a straight line, and a region 708 that includes fundamental image data (or harmonic image data). In this way, the region 704 that is proximal to the transition zone 706 may include one type of image data, and the region 708 that is distal to the transition zone 706 may include the other type of image data.

Figure 7B:
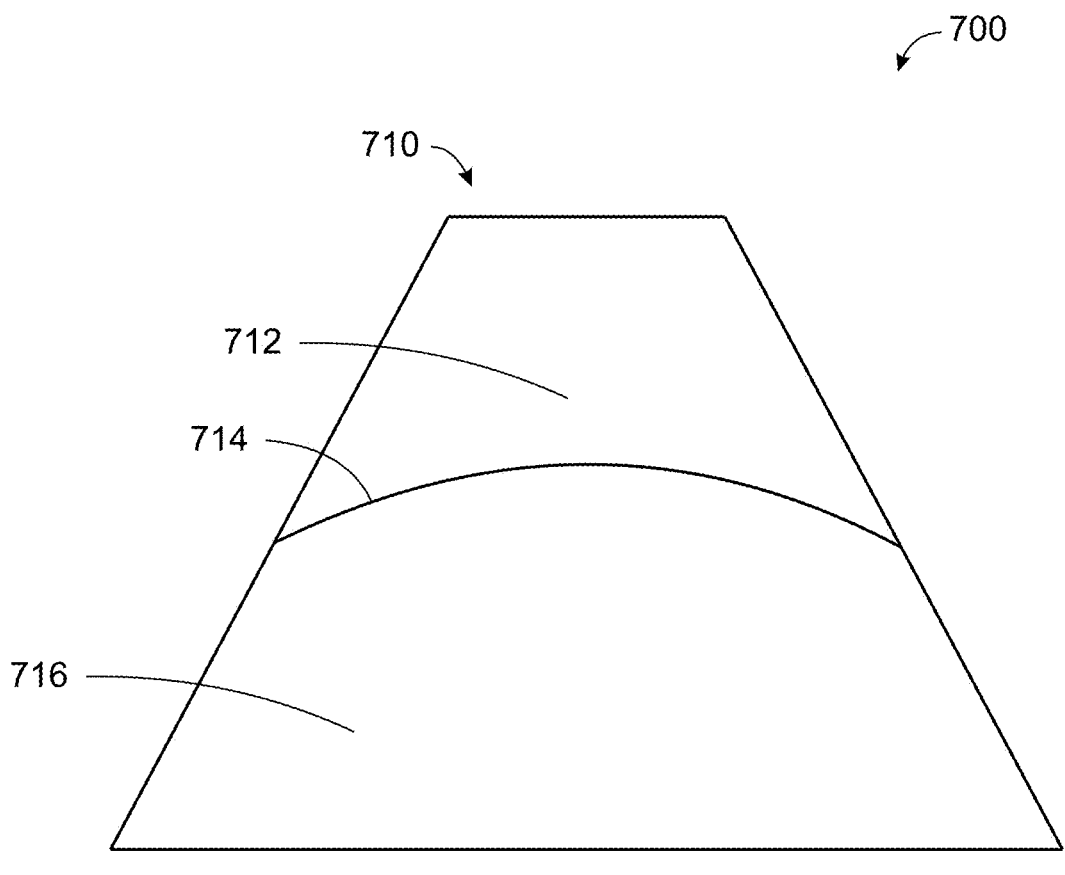
FIG. 7B is a diagram of an example transition zone in the form of a curved line.

FIG. 7B is a diagram of an example transition zone in the form of a curved line. As shown in FIG. 7B, the blended image 710 may include a region 712 that includes harmonic image data (or fundamental image data), a transition zone 714 in the form of a curved line, and a region 716 that includes fundamental image data (or harmonic image data). In this way, the region 712 that is proximal to the transition zone 714 may include one type of image data, and the region 716 that is distal to the transition zone 714 may include the other type of image data.

Figure 7C:
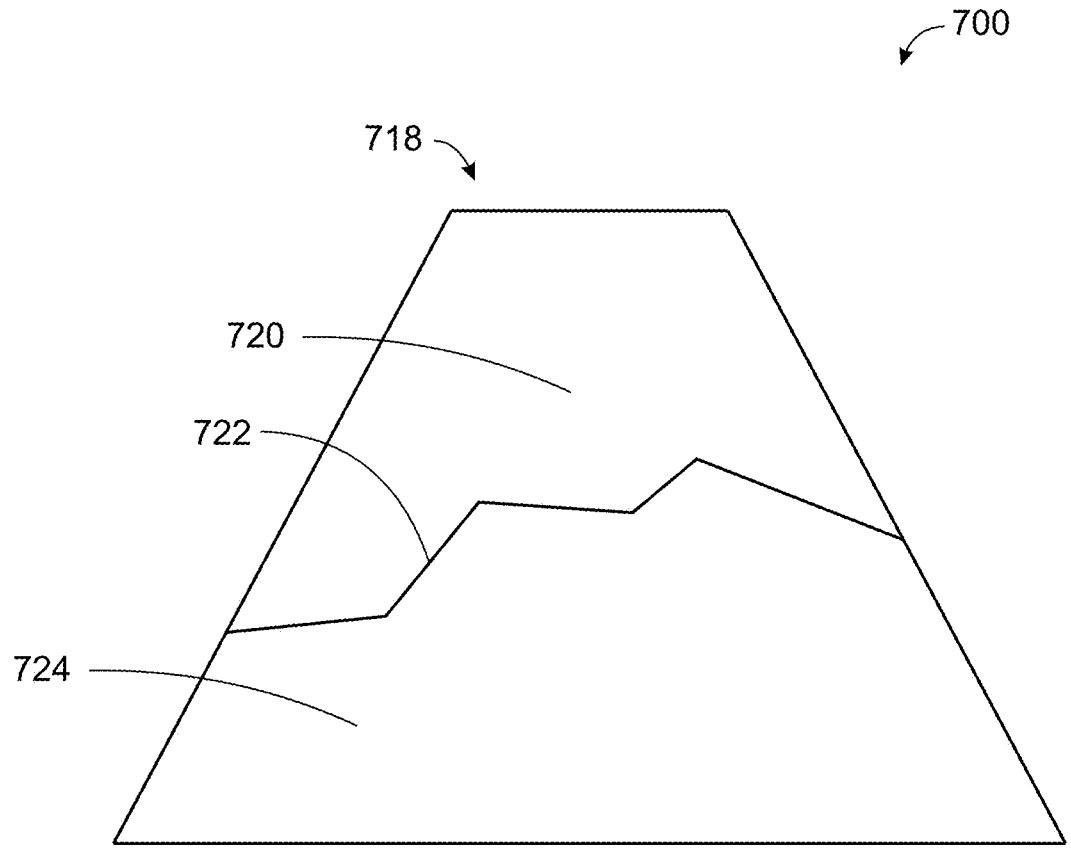
FIG. 7C is a diagram of an example transition zone in the form of a curved line.

FIG. 7C is a diagram of an example transition zone in the form of a curved line. As shown in FIG. 7C, the blended image 718 may include a region 720 that includes harmonic image data (or fundamental image data), a transition zone 722 in the form of a straight line, and a region 724 that includes fundamental image data (or harmonic image data). In this way, the region 720 that is proximal to the transition zone 722 may include one type of image data, and the region 724 that is distal to the transition zone 722 may include the other type of image data.

Figure 7D:
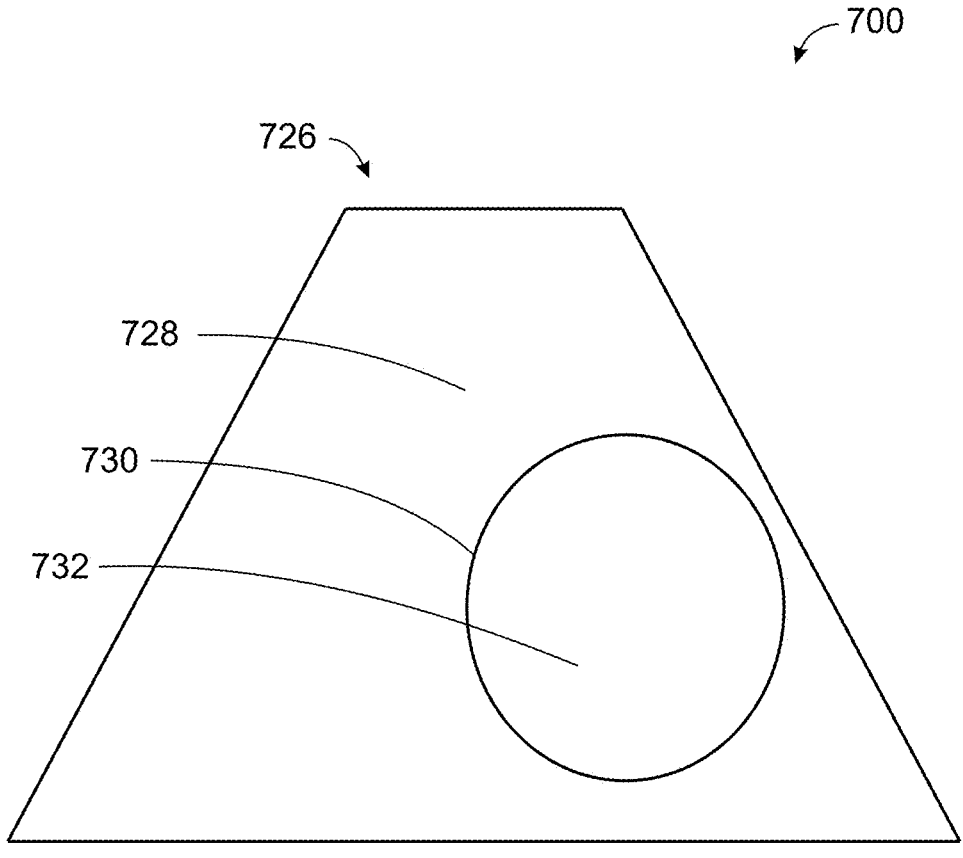
FIG. 7D is a diagram of example transition zones in the form of a circle.

FIG. 7D is a diagram of example transition zones in the form of a circle. As shown in FIG. 7D, the blended image 726 may include a region 728 that includes harmonic image data (or fundamental image data), a transition zone 730 in the form of a circle, and a region 732 that includes fundamental image data (or harmonic image data). In this way, the region 728 that is external to the transition zone 730 may include one type of image data, and the region 732 that is internal to the transition zone 730 may include the other type of image data.

Figure 7E:
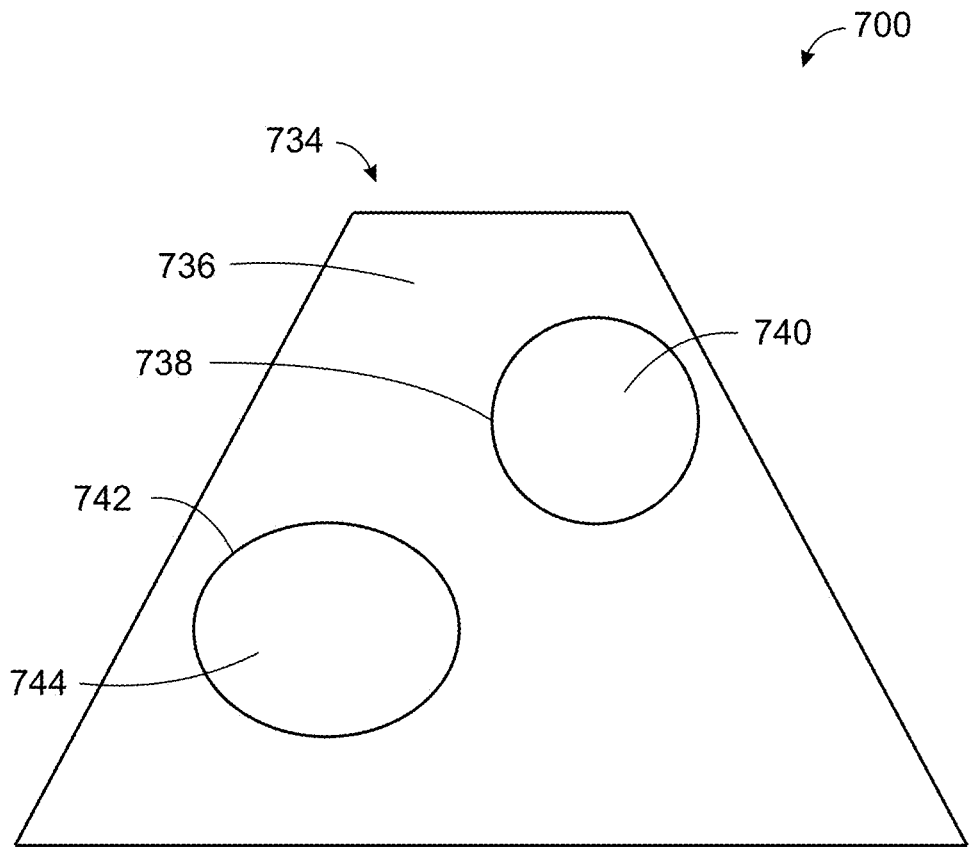
FIG. 7E is a diagram of an example transition zone in the form of circles.

FIG. 7E is a diagram of an example transition zone in the form of circles. As shown in FIG. 7D, the blended image 734 may include a region 736 that includes harmonic image data (or fundamental image data), a first transition zone 738 in the form of a circle, a region 740 that includes fundamental image data (or harmonic image data), a second transition zone 742, and a region 744 that includes fundamental image data (or harmonic image data). In this way, the region 736 that is external to the first transition zone 738 and the second transition zone 742 may include one type of image data, and the region 740 that is internal to the first transition zone 738 and the region 744 that is internal to the second transition zone 742 may include the other type of image data.

Although FIGS. 7A-7E depict transition zones having particular geometrical shapes, it should be understood that the transition zone may include any shape, pattern, or form. Further, although FIGS. 7A-7E depict a particular number of transition zones, it should be understood that the blended image may include any number of transition zones.

In this way, some implementations herein provide an ultrasound imaging system for generating a blended image including harmonic image data from a harmonic image and fundamental image data from a fundamental image based on determining a transition zone. The ultrasound imaging system may control an ultrasound probe to acquire a fundamental image of a region of interest of a subject, and control the ultrasound probe to acquire a harmonic image of the region of interest of the subject. The ultrasound imaging system may generate a blended image including harmonic image data from the harmonic image and fundamental image data from the fundamental image based on determining the transition zone, and control a display to display the blended image. The blended image may include improved quality by including high quality areas of the harmonic image and high quality areas of the fundamental image based on the determined transition zone. Further, the blended image may include an improved and more realistic appearance over situations in which a predetermined transition zone is utilized. In this way, some implementations herein provide a technical improvement in the technical field of ultrasound image, and provide a technical improvement to ultrasound images by generating a blended image that utilizes a determined transition zone.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. An ultrasound imaging system comprising:
an ultrasound probe;
a display; and
one or more processors configured to:
  control the ultrasound probe to acquire a fundamental image of a region of interest of a subject;
  control the ultrasound probe to acquire a harmonic image of the region of interest of the subject;
  generate a noise image based on noise image data acquired by the ultrasound probe;
  determine one or more values of the noise image that satisfy a threshold;
  determine a transition zone at which to blend the harmonic image and the fundamental image based on respective positions of the one or more values of the noise image that satisfy the threshold;
  generate a blended image including harmonic image data from the harmonic image and fundamental image data from the fundamental image based on determining the transition zone; and
  control the display to display the blended image.

2. The ultrasound imaging system of claim 1, wherein the one or more processors are further configured to:
  generate a time gain compensation (TGC) matrix based on TGC data acquired by the ultrasound probe,
  wherein the determining the transition zone comprises determining the transition zone based on the TGC matrix and the noise image.

3. The ultrasound imaging system of claim 1, wherein the one or more processors are configured to determine the transition zone using an artificial intelligence (AI) model.

4. The ultrasound imaging system of claim 1, wherein the transition zone is substantially horizontal.

5. The ultrasound imaging system of claim 1, wherein the transition zone includes a geometric shape.

6. The ultrasound imaging system of claim 1, wherein the one or more processors are further configured to:
  determine another transition zone,
  wherein the generating the blended image comprises generating the blended image based on the transition zone and the other transition zone.

7. A method comprising:
controlling an ultrasound probe to acquire a fundamental image of a region of interest of a subject;
controlling the ultrasound probe to acquire a harmonic image of the region of interest of the subject;
generating a noise image based on noise image data acquired by the ultrasound probe;
determining one or more values of the noise image that satisfy a threshold;
determining a transition zone at which to blend the harmonic image and the fundamental image;
generating a blended image including harmonic image data from the harmonic image and fundamental image data from the fundamental image based on determining the transition zone based on respective positions of the one or more values of the noise image that satisfy the threshold; and
controlling a display to display the blended image.

8. The method of claim 7, further comprising:
generating a time gain compensation (TGC) matrix based on TGC data acquired by the ultrasound probe,
wherein the determining the transition zone comprises determining the transition zone based on the TGC matrix and the noise image.

9. The method of claim 7, wherein the determining the transition zone comprises determining the transition zone using an artificial intelligence (AI) model.

10. The method of claim 7, wherein the transition zone is substantially horizontal.

11. The method of claim 7, wherein the transition zone includes a geometric shape.

12. The method of claim 7, further comprising:
determining another transition zone,
wherein the generating the blended image comprises generating the blended image based on the transition zone and the other transition zone.

13. A non-transitory computer-readable medium storing instructions that, when executed by one or more processors of an ultrasound imaging system, cause the one or more processors to:
  control an ultrasound probe to acquire a fundamental image of a region of interest of a subject;
  control the ultrasound probe to acquire a harmonic image of the region of interest of the subject;
  generate a noise image based on noise image data acquired by the ultrasound probe;

determine one or more values of the noise image that satisfy a threshold;

determine a transition zone at which to blend the harmonic image and the fundamental image;

generate a blended image including harmonic image data from the harmonic image and fundamental image data from the fundamental image based on determining the transition zone based on respective positions of the one or more values of the noise image that satisfy the threshold; and control a display to display the blended image.

14. The non-transitory computer-readable medium of claim 13, wherein the one or more processors are further configured to:

generate a time gain compensation (TGC) matrix based on TGC data acquired by the ultrasound probe, wherein the determining the transition zone comprises determining the transition zone based on the TGC matrix and the noise image.

15. The non-transitory computer-readable medium of claim 13, wherein the one or more processors are configured to determine the transition zone using an artificial intelligence (AI) model.

16. The non-transitory computer-readable medium of claim 13, wherein the transition zone is substantially horizontal.

17. The non-transitory computer-readable medium of claim 13, wherein the transition zone includes a geometric shape.

* * * * *